US011464656B2

(12) United States Patent
Donovan et al.

(10) Patent No.: US 11,464,656 B2
(45) Date of Patent: Oct. 11, 2022

(54) POST-OPERATIVE SUPPORT APPARATUS FOR A PATIENT'S RESIDUAL LIMB

(71) Applicant: Cobblestone, LLC, Cumberland, ME (US)

(72) Inventors: John-Paul Donovan, Cumberland, ME (US); Shannon Donovan, Cumberland, ME (US); Mitchel Donovan, Cumberland, ME (US)

(73) Assignee: Cobblestone, LLC, Cumberland, ME (US)

( * ) Notice: Subject to any disclaimer, the term of this patent is extended or adjusted under 35 U.S.C. 154(b) by 173 days.

(21) Appl. No.: 16/736,402

(22) Filed: Jan. 7, 2020

(65) Prior Publication Data

US 2020/0170810 A1 Jun. 4, 2020

Related U.S. Application Data

(63) Continuation-in-part of application No. 15/247,507, filed on Aug. 25, 2016, now Pat. No. 10,524,937.

(60) Provisional application No. 62/211,318, filed on Aug. 28, 2015.

(51) Int. Cl.
*A61F 2/78* (2006.01)
*A61F 5/01* (2006.01)
*A61F 2/50* (2006.01)

(52) U.S. Cl.
CPC .............. *A61F 2/7812* (2013.01); *A61F 2/78* (2013.01); *A61F 5/0102* (2013.01); *A61F 5/0193* (2013.01); *A61F 2002/503* (2013.01); *A61F 2002/7862* (2013.01); *A61F 2002/7881* (2013.01); *A61F 2005/0183* (2013.01)

(58) Field of Classification Search
CPC .... A61F 2/78; A61F 2/7812; A61F 2002/503; A61F 2002/7818; A61F 2002/785; A61F 2002/7862; A61F 2002/7881; A61F 5/0102; A61F 5/0106; A61F 5/0193; A61F 2005/0183; A61F 5/0109; A41F 11/00; A41F 11/16
See application file for complete search history.

(56) References Cited

U.S. PATENT DOCUMENTS

| 4,013,070 | A |   | 3/1977  | Harroff |               |
|-----------|---|---|---------|---------|---------------|
| 4,790,855 | A | * | 12/1988 | Jolly   | ........... A61F 2/78 |
|           |   |   |         |         | 623/32        |
| 5,076,288 | A | * | 12/1991 | Millard | ........ A61F 5/3776 |
|           |   |   |         |         | 128/869       |
| 6,131,206 | A | * | 10/2000 | Vayda   | ........ A41F 11/00 |
|           |   |   |         |         | 2/312         |

(Continued)

*Primary Examiner* — Keri J Nelson
(74) *Attorney, Agent, or Firm* — BakerHostetler (57) ABSTRACT

A post-operative support apparatus for a patient's transfemoral residual limb, includes: a planar, stretchable, tensionable and flexible wrap panel sized to wrap around an outer circumference of a patient's transfemoral residual limb, where the wrap panel includes first fastener(s) for maintaining the wrap panel in place around the patient's residual limb; a planar, stretchable, tensionable and flexible hip-band sized to wrap around an outer circumference of a patient's hip or waist, where the hip-band includes second fastener(s) for maintaining the hip-band in place around the patient's hip or waist; and third fastener(s) releasably fastening the wrap panel to the hip-band.

1 Claim, 11 Drawing Sheets

(56) References Cited

U.S. PATENT DOCUMENTS

| | | | |
|---|---|---|---|
| 6,652,596 B2* | 11/2003 | Smith | A61F 2/60 2/22 |
| 8,679,193 B2 | 3/2014 | Astilla et al. | |
| 8,827,941 B2 | 9/2014 | Davis et al. | |
| 2010/0292622 A1* | 11/2010 | Weissleder | A61F 5/0193 602/23 |
| 2017/0056250 A1* | 3/2017 | Donovan | A61F 2/7812 |
| 2020/0008495 A1* | 1/2020 | Anderson | A41D 13/0525 |

* cited by examiner

POST-OPERATIVE SUPPORT APPARATUS FOR A PATIENT'S RESIDUAL LIMB

CROSS REFERENCE TO RELATED APPLICATIONS

The current application is a continuation-in-part of, and claims priority to, U.S. patent application Ser. No. 15/247,507 filed on Aug. 25, 2016 and titled "POST-OPERATIVE SUPPORT APPARATUS FOR A PATENT'S RESIDUAL LIMB," the entire disclosure of which is incorporated herein by reference, and which claims priority to U.S. Provisional App. Ser. No. 62/211,318, filed Aug. 28, 2015, the entire disclosure of which is incorporated herein by reference.

BACKGROUND

Following a patient's amputation, there is a need for a prosthetic limb post-operative support device that can be used to protect the patient's residual limb soon after the amputation and to help avoid any traumas to the limb so the limb can properly heal. Current known post-operative support apparatuses contain a hard plastic shell or socket that provides limited ability to accommodate a change in the volume or dimensions of the limb after the post-operative component is fit. Such hard plastic shells themselves may present a risk to, and may be the cause of, in some instances, damage to the sensitive soft tissues after the surgery.

Accordingly, there is a need for a post-operative assembly that has the ability to account for occasional swelling of the patient's residual limb, possible de-bulking of wound dressing, expected/possible atrophy in the patient's residual limb and other changes to the volume or shape of the patient's residual limb as the limb heals following the operation. For example, it is common that the residual limb and dressing can lose upwards of 50 percent of its volume in the 48 hours following the amputation surgery.

SUMMARY

Embodiments of the current disclosure may be directed to a post-operative support apparatus for a patient's residual limb. The apparatus includes: a planar, stretchable and flexible wrap panel sized to wrap around an outer circumference of a patient's residual limb, along a length of the patient's residual limb, where the wrap panel includes one or more fasteners (such as hook & loop fastener components) for maintaining the wrap panel in place around the patient's residual limb; a pair of substantially rigid, elongated side support panels to respectively apply to the medial and lateral sides of the patient's residual limb, over the wrap panel; a distal cushion to apply against a distal end of the patient's residual limb; and a retainer maintaining the distal cushion against the patient's residual limb.

In such embodiments, the retainer may be a planar, stretchable and flexible distal panel to apply against the distal end of the distal cushion, and including a plurality of legs extending therefrom to extend proximally up against an outer surface of the wrap panel, where each of the plurality of legs include fasteners (such as hook & loop fastener components) for maintaining the legs against the outer surface of the wrap panel. Further, in such embodiments, the retainer includes four legs in a cross-shaped arrangement.

In such embodiments, the wrap panel may be formed from a neoprene material. Further, the distal panel may be formed from a neoprene material.

Such embodiments may further include a suspensory strap to be applied circumferentially around the outer surface of the wrap panel. In further detailed embodiments, the suspensory strap is to be applied above the supracondylar aspect of the femur of the patient's residual limb so as to provide suspension of the post-operative support apparatus from falling distally off the patient's residual limb. Further, the suspensory strap may include a fastener(s) (such as a hook & loop fastener component(s)) maintaining the suspensory strap about the outer surface of the wrap panel and creating a closure to the circumferential strap itself.

In such embodiments, the pair of substantially rigid, elongated side support panels may include planar, elongated thermoplastic panels. Further, in such embodiments, the pair of substantially rigid, elongated thermoplastic panels may reside in sleeves or pockets made from a stretchable and flexible material such as neoprene for example.

In such embodiments, the wrap panel may each include an outer layer of cloth material susceptible to engaging with a hook component of a hook and loop fastener.

A more detailed embodiment of the current disclosure is directed to a post-operative support apparatus that includes: (a) a planar, wrap panel sized to wrap around an outer circumference of a patient's residual limb, along a length of the patient's residual limb, where the wrap panel includes a layer of neoprene material, an outer layer of cloth material and a plurality of tabs extending from a longitudinal side edge, where the tabs including loop components of a hook and loop fastener for fastening to the outer layer of cloth material of the wrap panel and maintaining the wrap panel in place around the patient's residual limb; (b) a pair of substantially rigid, elongated side support panels residing in sleeves, the sleeves including at least one loop component of a hook and loop fastener attached to at least one planar side of the sleeve for fastening the sleeve and the side support panel to the cloth outer layer of the wrap panel, respectively on the medial and lateral sides of the patient's residual limb; (c) a suspensory strap to be applied circumferentially around the outer surface of the wrap panel above the supracondylar aspect of the femur of the patient's residual limb so as to provide suspension of the post-operative support apparatus from falling distally off the patient's residual limb; (d) a distal cushion with a concave proximal surface to apply against a distal end of the patient's residual limb; and (e)(c) a flexible, planar distal panel to apply against the distal end of the distal cushion, and including a plurality of flexible legs extending therefrom to extend proximally up against the outer layer of cloth material of the wrap panel, where each of the plurality of legs include one or more loop components of hook and loop fasters for fastening to the outer layer of cloth material of the wrap panel and maintaining the legs against the outer surface of the wrap panel.

Embodiments of the current disclosure also include a method for donning a post-operative support apparatus to a residual limb, comprising the steps of: (a) obtaining any of the post-operative support apparatuses as summarized above; (b) wrapping the wrap panel around the patient's residual limb and fastening the first fasteners to close the wrap panel about the patient residual limb; (c) fastening the suspensory strap to circumferentially around the outer surface of the wrap panel above the supracondylar aspect of the femur of the patient's residual limb so as to provide suspension of the post-operative support apparatus from falling distally off the patient's residual limb; (d) fastening the side support panels respectively on the medial and lateral sides of the patient's residual limb, where the elongated side support panels extend vertically along the patient's residual limb; (e)

positioning the distal cushion to the distal end of the patient's residual limb; and (f) positioning the planar distal panel over the distal cushion and fastening the plurality of legs of the planar distal cushion to the outer surface of the wrap panel to thereby retain the distal cushion to the distal end of the patient's residual limb. It is to be understood that the above steps are not required to be performed in order. For example, and without limitation, step (c) for fastening the suspensory strap can occur later in the method, step (d) for fastening the side support panels can occur earlier or later in the method, and steps (d) & (e) for positioning and fastening the distal cushion and distal panel can occur earlier in the method.

In an alternate embodiment, a post-operative support apparatus for a patient's transfemoral residual limb, includes: a planar, stretchable, tensionable and flexible wrap panel sized to wrap around an outer circumference of a patient's transfemoral residual limb, where the wrap panel includes first fastener(s) for maintaining the wrap panel in place around the patient's residual limb; a planar, stretchable, tensionable and flexible hip-band sized to wrap around an outer circumference of a patient's hip or waist, where the hip-band includes second fastener(s) for maintaining the hip-band in place around the patient's hip or waist; and third fastener(s) releasably fastening the wrap panel to the hip-band. In a more detailed embodiment, the post-operative support apparatus may further include a planar, stretchable, tensionable and flexible distal panel including fourth fastener(s) releasably fastening the distal panel to a distal end of the wrap panel and over the distal end of the patient's transfemoral residual limb. In a further detailed embodiment, the apparatus may further include a distal cushion between the distal panel and the distal end of the patient's residual limb.

Alternatively, or in addition, the hip-band of the alternate embodiment includes a central panel segment configured for orienting about a side of a patient's hip and a waist-band segment for wrapping about the patient's hip or waist, and the second fastener(s) releasably fasten a leading end the waist-band segment to the central panel segment. In a further detailed embodiment, the central panel segment and the waist-band segment are separate components releasably coupled together at a trailing end of the waist-band segment by fourth fastener(s). Alternatively, the central panel segment and the waist-band segment are a unitary component. Alternatively, or in addition, the central panel segment includes an outer layer of cloth material susceptible to engaging with a hook component of a hook and loop fastener, and the second fastener(s) include a hook component of a hook and loop fastener. Alternatively, or in addition, the central panel is generally triangular. Alternatively, or in addition, the central panel includes a central hole extending therethrough adapted to register upon a portion of a patient's hip.

Alternatively, or in addition, the third fastener(s) of the alternate embodiment include an inner fastening tab and at least one outer fastening tab sandwiching the wrap panel therebetween. Alternatively, or in addition, the apparatus further includes a plurality of the outer fastening tabs. Alternatively, or in addition, the inner fastening tab is wider than the at least one outer fastening tab. Alternatively, or in addition, the hip-band includes a central panel segment configured for orienting about a side of a patient's hip and a waist-band segment for wrapping about the patient's hip or waist; the second fastener(s) releasably fasten a leading end the waist-band segment to the central panel segment; the central panel segment includes a distal end width and a proximal end width, the distal end width being larger than the proximal end width; and the inner fastening tab extends the substantially the entire distal end width of the central panel segment. In a further detailed embodiment, the inner fastening tab is wider than the distal end width of the central panel segment. Alternatively, or in addition, the central panel includes reinforcement along at least a partial length of the proximal end. Alternatively, or in addition, the waist-band segment includes reinforcement along at least a partial length of the waist-band segment.

Embodiments of the current disclosure include a method for donning a post-operative support apparatus to a transfemoral residual limb that the steps of: providing a post-operative support apparatus including (a) a planar, stretchable, tensionable and flexible wrap panel sized to wrap around an outer circumference of a patient's transfemoral residual limb, the wrap panel including first fastener(s) for maintaining the wrap panel in place around the patient's residual limb; (b) a planar, stretchable, tensionable and flexible hip-band sized to wrap around an outer circumference of a patient's hip or waist, the hip-band including second fastener(s) for maintaining the hip-band in place around the patient's hip or waist; and (c) third fastener(s) releasably fastening the wrap panel to the hip-band; wrapping the wrap panel around the patient's residual limb and fastening the first fasteners to close the wrap panel about the patient's residual limb; wrapping the hip-band around the patient's hip or waist and fastening the second fasteners to close the hip-band around the patient's hip or waist; and fastening the third fasteners to couple the wrap panel to the hip-band. The steps following the providing step may occur in any order. In a more detailed embodiment, the method may further include a step of trimming away one or more portions of the wrap panel based upon dimensions of the patient's residual limb. In a further detailed embodiment, the trimming step occurs upon a re-fitting of the wrap panel to the patient's residual limb to adjust for dimensional changes to the patient's residual limb after an initial fitting. In a further detailed embodiment, the trimming step is performed by scissors cutting away the one or more portions of the wrap panel.

These and other aspects of the current disclosure will be apparent from the following detailed discussion, the appended claims and the attached figures.

DETAILED DESCRIPTION OF THE DISCLOSED EMBODIMENTS

Figure 1:
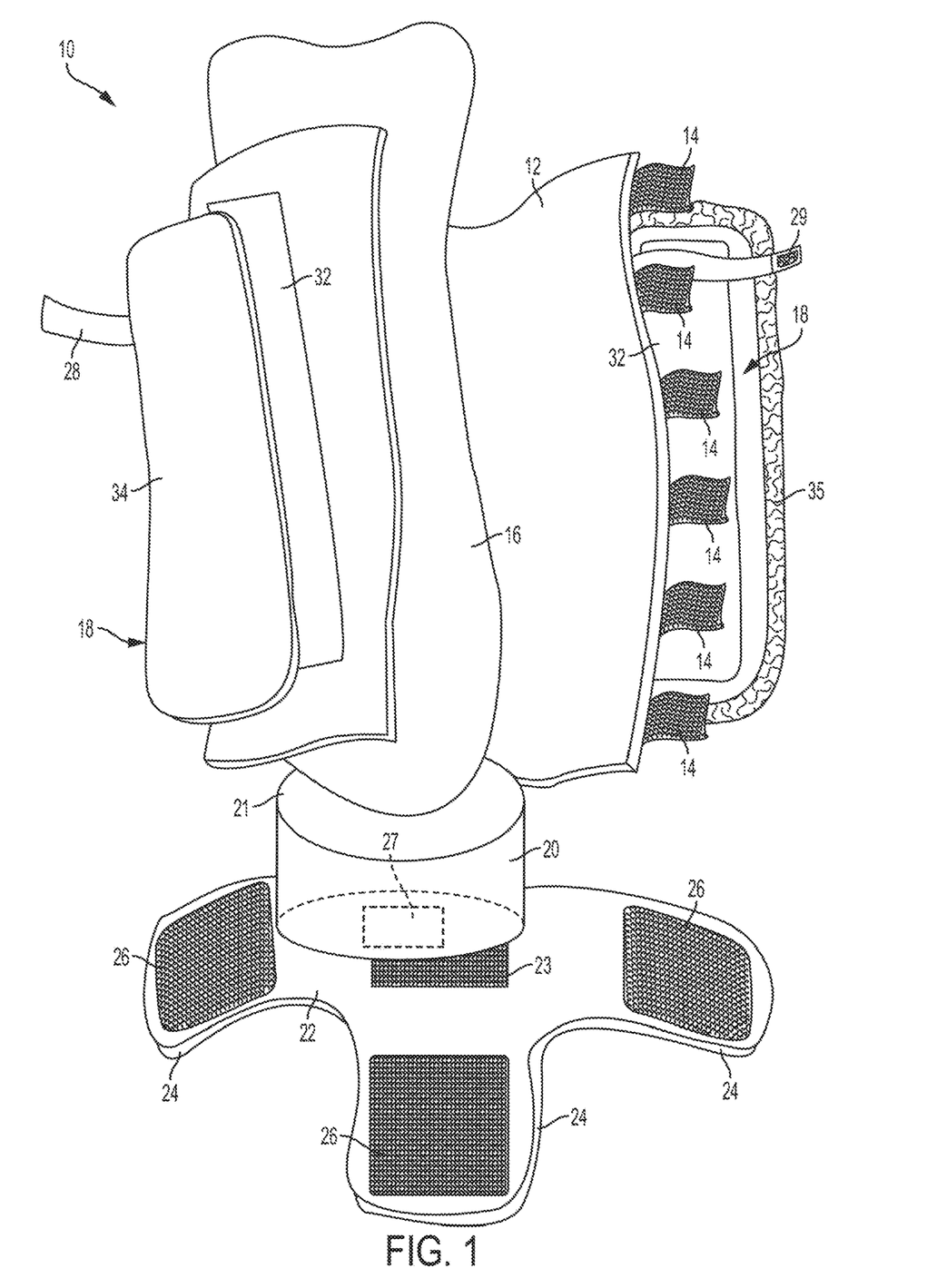
FIG. 1 is an exploded perspective view of an embodiment of a below-knee post-operative support apparatus according to the current disclosure.
Figure 2:
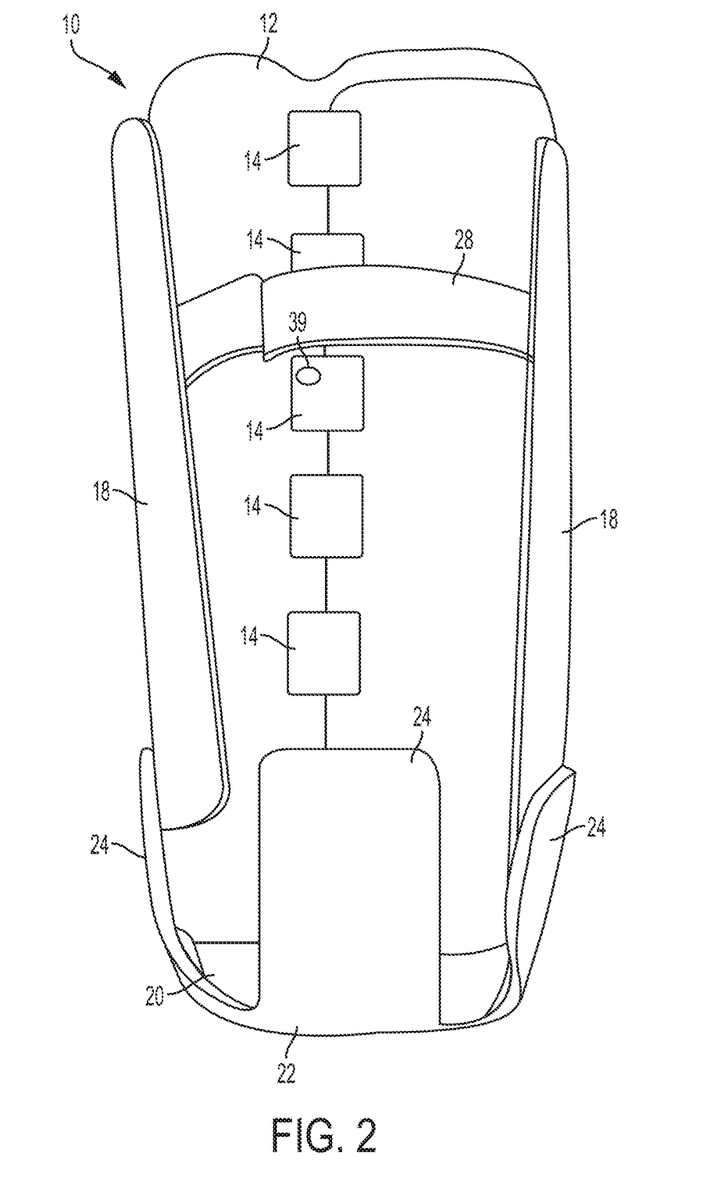
FIG. 2 is a perspective assembled view of the embodiment of FIG. 1.
Figures 3, 4:
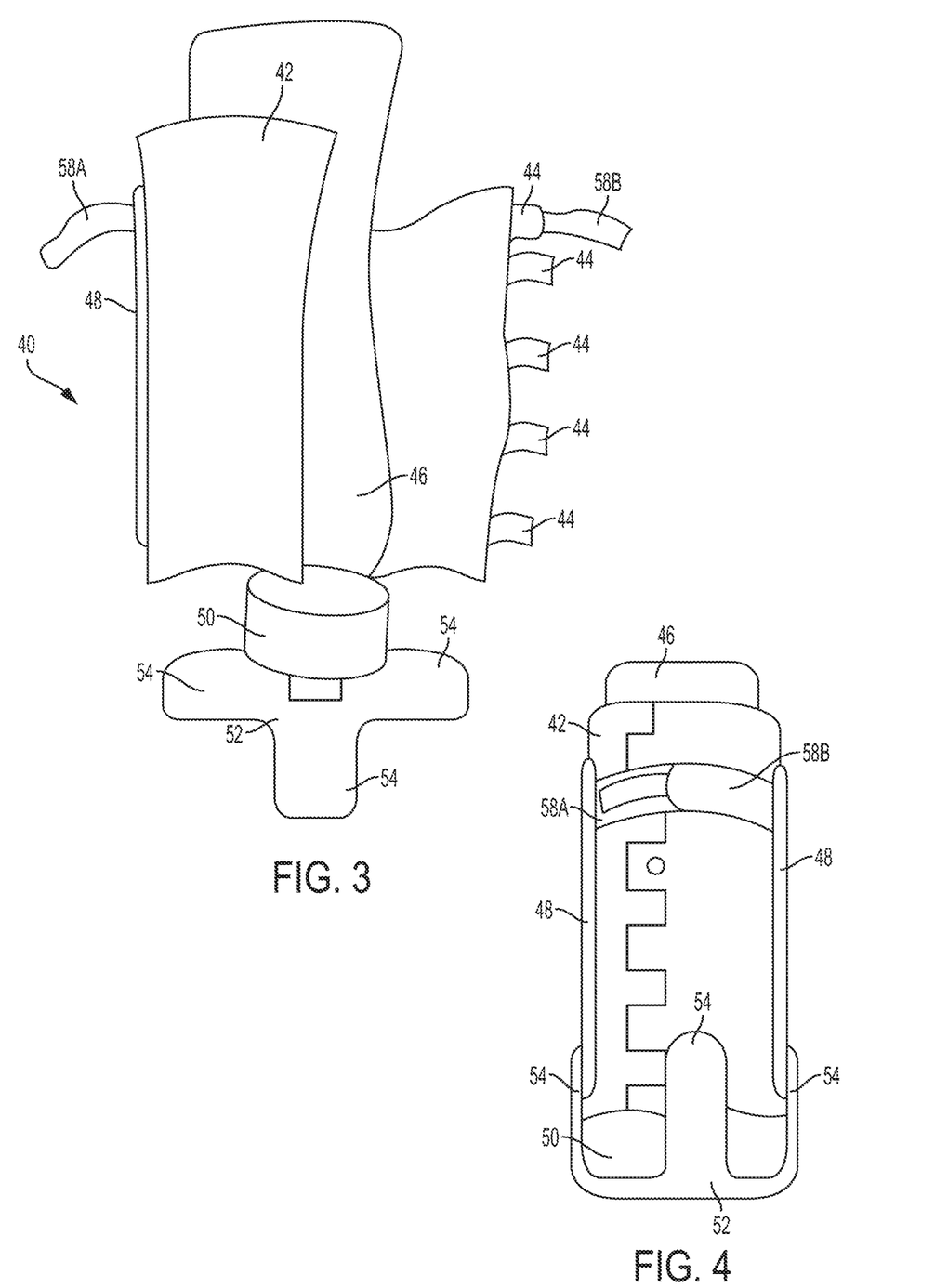
FIG. 3 is an exploded perspective view of another embodiment of a below-knee post-operative support apparatus according to the current disclosure.
FIG. 4 is a perspective assembled view of the embodiment of FIG. 3.
Figure 5:
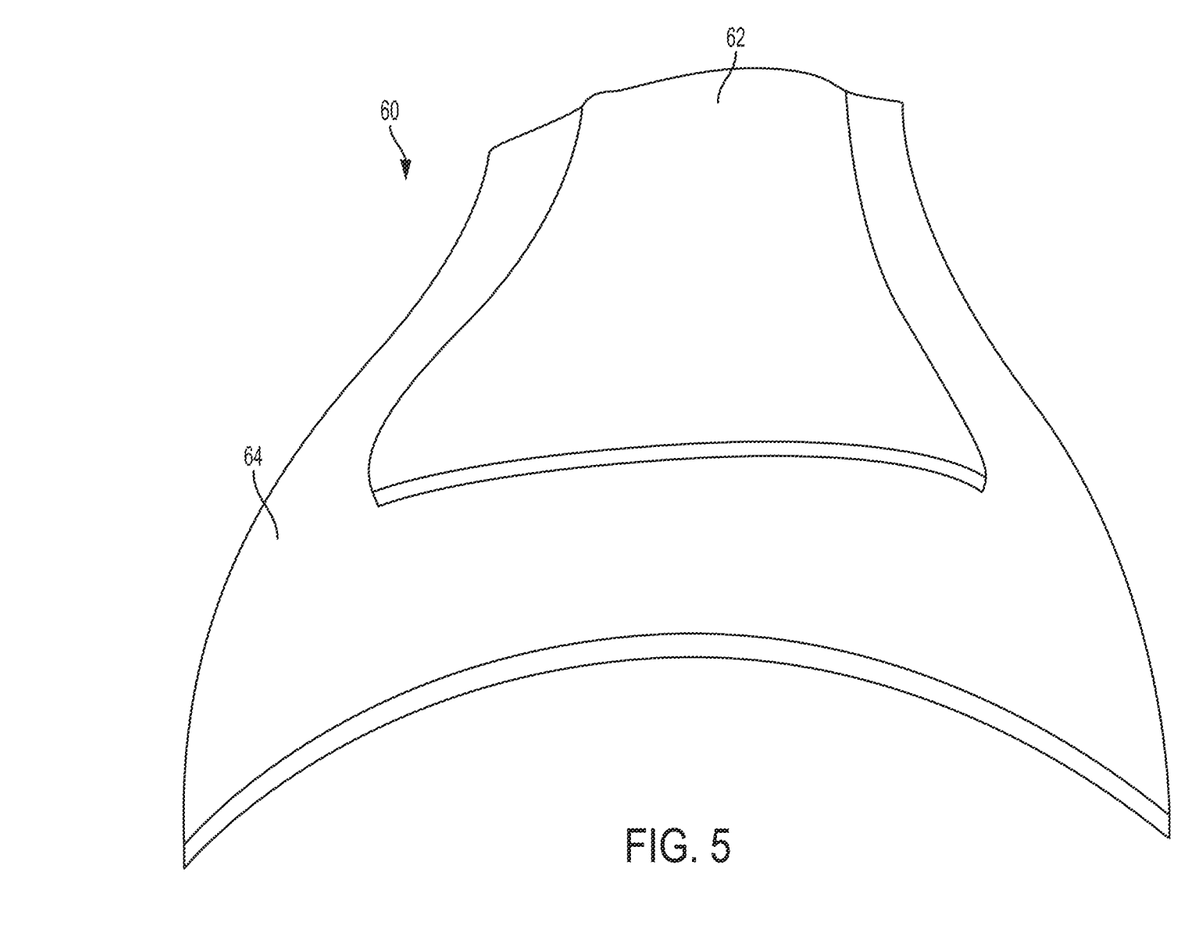
FIG. 5 is a perspective view of an alternate side assembly for use with post-operative support apparatuses as disclosed herein.
Figure 6A:
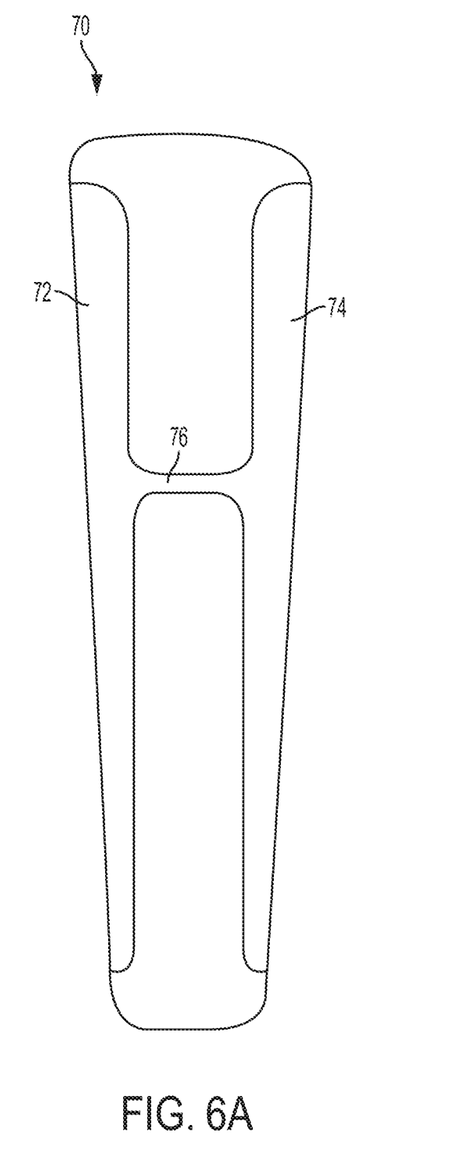
FIG. 6A is a back view of another alternate side assembly for use with post-operative support apparatuses as disclosed herein.
Figure 6B:
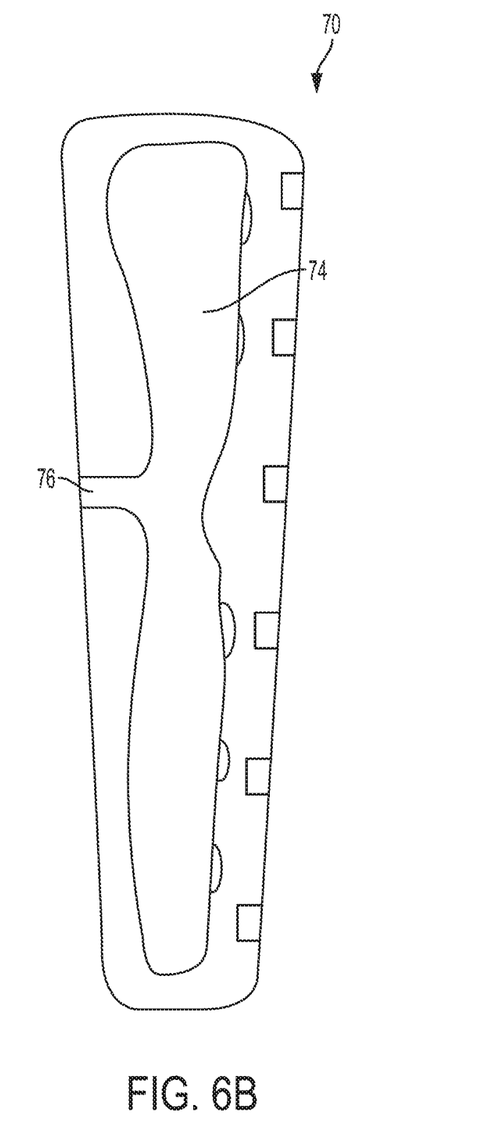
FIG. 6B is a side view of the alternate side assembly of FIG. 6A.

FIGS. 1 and 2 illustrate various components of a first example embodiment of a below-knee post-operative support apparatus according to the current disclosure, as well as various steps for using the first embodiment and donning the first embodiment on a patient's residual limb soon after amputation. FIGS. 3 and 4 provide an alternate example embodiment a post-operative support apparatus according to the current disclosure, along with illustrations of its various components and steps for donning this embodiment onto the patient's residual limb soon after amputation. FIGS. 5, 6A and 6B provide alternate embodiments of the elongated side support panel assemblies for use with post-operative support apparatuses as discussed herein.

Referring to FIGS. 1 and 2, a first exemplary embodiment of the post-operative support apparatus 10 includes a planar, flexible and stretchable wrap panel 12 that is sized to wrap around an outer circumference of the patient's residual limb 16, along a length of the patient's residual limb. In this embodiment, the wrap panel 12 may include an inner layer of neoprene material and an out layer of terry cloth material. In the exemplary embodiment, the neoprene material may be nylon lined and perforated (ventilation may promote dissipation of moisture and create airflow to assist in patient comfort and wound healing). The planar wrap panel 12 may also include a plurality of tabs 14 extending from a longitudinal side edge of the wrap panel where the tabs include loop hook components of a hook and loop fastener system (Velcro® fastener), where the loop hook components will fasten to the outer layer of terry cloth material of the wrap panel 12 to maintain the wrap panel in place wrapped around the patient's residual limb 16.

The current embodiment 10 may also include a pair of substantially rigid, elongated side support panel assemblies 18. In this embodiment each elongated side support panel assembly 18 includes an outer sleeve 34 of neoprene material and a planar, elongated thermoplastic panel 32 that is received within the sleeve 34 (in this embodiment, the thermoplastic panel 32 is seated between the outer sleeve 34 and the outer surface of the planar wrap panel 12 when the outer sleeve 34 is fastened to the outer surface of the planar wrap panel 12 with the thermoplastic panel 32 positioned therebetween). Each of the sleeve assemblies 18 include a layer 35 of hook components of a hook and loop fastener system (Velcro system) distributed about the periphery of the inner surface of the elongated side support panel assembly 18. This layer 35 of hook components allow the elongated side support panel assemblies 18 to be fastened to the terry cloth material on the outer surface of the planar wrap panel 12 once the wrap panel has been wrapped around the patient's residual limb 16.

The current embodiment 10 of the post-operative support apparatus also includes a suspensory strap 28 that is wrapped circumferentially around at least a portion the outer surface of the wrap panel 12 and elongated side support assemblies 18 after the wrap panel has been wrapped around the patient's residual limb 16 (but, preferably, before the panel assemblies 18 have been fastened to the outer surface of the wrapped panel 12). The suspensory strap also includes an inner layer of neoprene material and an outer layer of terry cloth material as well as a patch of loop component material 29 extending from a longitudinal end and on the inner surface thereof. In this configuration, the suspensory strap can be wrapped around the wrap panel 12 and then fastened by applying the loop component patch 29 to the outer terry cloth material on the outer surface of the suspensory strap 28. In an embodiment, the suspensory strap 28 is applied above the super condylar aspect of the femur of the patient's residual limb so as to provide suspension of the post-operative support apparatus 10 from falling distally off the patient's residual limb 16.

The current embodiment of the post-operative support apparatus 10 further includes a distal cushion component 20 with a concave proximal surface 21 that is applied against the distal end of the patient's residual limb. Thereafter, a flexible and stretchable planar distal panel 22 is applied against the distal end of the distal cushion 20. In an embodiment, the distal end of the cushion 20 includes a hook or a loop component patch 27 of a hook and loop fastener system (shown in phantom in FIG. 1 as being positioned on the underside of the cushion 20) and the distal panel 22 includes the corresponding loop or hook patch 23 to allow the distal panel 22 to fasten to the distal surface of the distal cushion 20. The flexible, planar distal panel 22 also includes a plurality of flexible legs 24 extending therefrom. Each of the legs have a patch of loop component material 26 fastened to the inner surface. In such a configuration, the legs may be pulled up vertically against the outer layer of terry cloth material of the wrap panel 12 after it has been wrapped around the patient's residual limb 16 to fasten the legs 24 against the outer surface of the wrap panel 12 and further maintain the distal panel 22 and distal cushion 20 to the overall assembly 10 about the patient's residual limb 16. The planar distal panel 22 may have an inner layer of neoprene material and an outer layer of terry cloth material, similar to the construction of the wrap panel 12. In the current embodiment, the distal panel 22 includes four of the legs 24 extending from the distal panel 22 in a cross-type configuration.

In a detailed embodiment, the planar wrap panel is substantially square, measuring 25 inches in length and 25 inches in width. In a detailed embodiment, the interior surface of the planar wrap panel 12 is made of a neoprene material with a hypo-allergenic nylon covering (perforated) and the exterior surface is formed from a Velcro-sensitive (hook sensitive) terry cloth covering. In a detailed embodiment, the side supports measure 3 inches in width by 20 inches in length, and $1/16^{th}$ of an inch in thickness, and are made from $1/16^{th}$-inch modified polyethylene material. In a detailed embodiment, the planar distal panel 22 measures 14½ inches from end to end of each leg 24 and the center Velcro patch 23 is 2 inches in width and 2½ inches in length.

In a detailed embodiment, the suspensory strap is 2 inches in width by 25 inches in length and made from $1/8^{th}$-inch neoprene material. The suspensory strap also includes a 2-inch by 3-inch patch 29 of Velcro hook component material. In such an embodiment, the suspensory strap 28 is designed for primary suspension at super condylar level of femur on the thigh. Circumferential stretch in the neoprene material decreases risk of circulatory compromise in case of over tightening. In a detailed embodiment, each patch of hook material 26 has a width of approximately 3½ inches and a length of about 4 inches. In this embodiment, the patch 26 does not extend all the way to the end of the leg 24 to allow for an end portion of the leg to be used as a tab that a patient may grip when applying or removing the leg 24. In a detailed embodiment, the hook tabs 14 are ½ inch wide.

In a detailed embodiment, the sleeve component 34 is constructed of a layer of neoprene material having an outer surface of a terry cloth material. The inner surface of the neoprene material has a patch 35 of hook component cemented about its periphery. Because the hook component material 35 is only at the periphery of the sleeve component 34 in this embodiment, when the sleeve component 34 is fastened to the terry cloth material on the outer surface of the wrap panel 12, a pocket is formed between the outer surface of the wrap panel 12 in the inner surface of the sleeve component 34 inside the outer periphery of hook patches 35. Within that pocket, the plastic side support panels 32 are seated. As shown in these figures, each sleeve component measures 22 inches in length, is 4 inches in width, and is constructed from ⅛-inch nylon covered neoprene material.

In a detailed embodiment, the distal end of the distal cushion includes a patch 27 of hook and loop fastener material to mate with the opposing patch 23 on the planar distal panel 22. This distal cushion 20 is pre-molded for the patient's transtibial residual limb. It is designed to protect the sensitive residual limb post-operatively from potential trauma that could be sustained in a fall or by bumping the limb. It is also desired to achieve total contact with the residual limb because compression and resistance to swelling are important functions in post-operative healing. In this embodiment, the cushion 20 is cylindrical 2 inches thick and 6 inches in diameter. It includes a moisture barrier layer on the proximal side 21 to help the cushion 20 avoid absorbing fluid from the residual limb.

Next, various example steps in donning the first exemplary embodiment of the post-operative support apparatus 10 will be discussed. Starting off, the wrap panel 12 is first placed against the patient's residual limb 16 and the hook tabs 14 can be set on either the right or left side, often depending upon hand dominance of the patient or preference of the patient. Preferably, the lower end of the panel 12 is brought to the very bottom of the patient's residual limb 16.

Next, the panel 12 can be sized and trimmed based upon the patient's limb dimensions. For example, scissors may be used to trim the wrap panel so that there is only about a 2-inch overlap between the lateral side edges. Additionally, the top and bottom edges of the wrap panel may also be trimmed with scissors as necessary. Once trimmed, the wrap panel 12 is wrapped around the patient's residual limb such that the tabs fastened to the outer terry cloth surface of the wrap panel. Once the wrap panel 12 is wrapped around the patient's residual limb 16, it is desired to have the patient's residual limb located at the bottom end of the wrap panel 12. It is noted that the panel 12 may be wrapped about the patient's residual limb 16 so as to have a left-side opening or right-side opening depending upon patient preference. The current embodiment illustrates a left-side opening.

The above trimming steps may also be re-performed from time-to-time in response to the patient's residual limb changing and/or losing volume following an initial fitting of the device.

The next step is to secure the suspensory strap around the wrapped panel 12. In an embodiment, the suspensory strap 28 is fastened above the super condylar aspect of the femur of the patient's residual limb so as to provide suspension of the post-operative support apparatus 10 from falling distally off the patient's residual limb. The panel 12 may also include an indicator 39, such as a white dot, placed on the outer surface (such as on an outer surface of a tab 14) to indicate a position on the patient's residual limb to which the indicator 39 should be aligned for proper fitting. For example, the indicator may be positioned to be aligned with a patient's knee cap to assist patients and/or caregivers for proper alignment during donning and fitting. In an embodiment, the indicator 39 is positioned such that the distal end of the residual limb 16 is aligned with the inferior or bottom edge of the panel 12.

A next step is to fasten the side support assemblies 18 to the medial and lateral sides of the patient's residual limb over the wrap panel 12 and suspensory strap 28. In this step, the plastic support panels 32 are placed within the hook patches 35 that are applied around the periphery of the sleeve components 34. Additionally, the sleeves 34 and support panels 32 may be trimmed to length with scissors by first aligning them with a point ½ inch below the proximal lateral trim line and medial trim line of the device 10 respectively. Once trimmed, the panels 32 are pocketed into place as the sleeves 34 adhere their hook patches to the exterior terry cloth of the wrap panel 12.

A next step is to secure the distal cushion 20 and planar distal panel 22 to the distal end of the patient's residual limb 16. The corresponding patches of hook and loop fastener components 23/27 respectively on the distal end of the cushion 20 and on the inner surface of the distal planar panel 22 are fastened to each other so that the distal end of the cushion 20 is fastened to the middle of the inside surface of the distal planar panel 22. Then the concave proximal surface 21 of the cushion 20 is placed against the distal end of the residual limb 16; and then the legs 24 are pulled up (to apply snug tension) against the outer surface of the planar wrap 12 that is wrapped around the residual limb and/or the outer surfaces of the support panel assemblies 18 so that the loop component patches 26 on the underside of the legs 24 adhere to the terry cloth material on the outer surfaces of the planar wrap 12 and/or support panel assemblies 18. If necessary, the suspensory strap 28 can be re-secured with snug tension to provide primary suspension over the femoral condyles.

FIGS. 3 and 4 illustrate a second embodiment of the post-operative support assembly 40. In this embodiment, the side support panel assemblies 48 are sewn or otherwise permanently attached to the planar wrap panel 42; and two suspensory strap components 58A and 58B are also sewn or otherwise attached to the planar wrap panel 42 along vertical edges of the wrap panel approximate the proximal end of the wrap panel 42. Tabs 44, cushion 50, and planar distal panel 52 are essentially the same as tabs 14, cushion 20 and distal panel 22 in the first embodiment 10. To don the support assembly, the wrap panel is first wrapped around the patient's residual limb such that the tabs 44 overlap and secure to the outer surface of the panel on the front of the limb and so that the support panel assemblies 48 are positioned respectively over the medial and lateral sides of the patient's residual limb. Next, the cushion 50 and planar distal panel 52 are fastened as in the first embodiment. Next, the two suspensory strap components 58A and 58A are snugly secured (by hook and loop fasters) in an overlapping fashion to aid suspension. FIG. 4 shows the alternate embodiment 40 in a finished state.

With respect to the above embodiments, it will be understood that the side support panels 32 and/or the suspensory strap 28 may be integrated into the construction of the wrap panel 12 (as shown in the embodiment of FIGS. 3 and 4). Also, the side support panels 32 may be included without the neoprene sleeve 34 and/or the side support panels 32 may be applied to the patient's residual limb 16 prior to the wrap panel 12 being donned. FIG. 5 illustrates one such alternate construction 60 for the side support assemblies. This alternate construction 60 includes a molded thermoplastic panel 62 fastened (via hook & loop fasteners, for example) to a base layer 64 of nylon material. The molded panel 62 may be molded according to the shape and dimensions of the patient's residual limb (for example, the panel 62 may be molded over a positive cast of the patient's residual limb); as such, the molded panel 62 may have a slight concavity on the inner side. The molded panel 62 may also be able to be trimmed to the length of the residual limb and/or adjusted to the circumference of the residual limb. FIGS. 6A and 6B illustrate another such alternate construction 70 for the side support assemblies. This alternate construction 70 is essentially a one-piece thermoplastic unit that includes two side-panel segments 72, 74 and a connecting bridge-segment 76 that laterally extends horizontally between and behind (e.g., behind the knee) the two side-panel segments about the back-side of the patient's residual limb. This construction 70 may be molded thermoplastic component that is allowed to bend, yield and contour to the limb, but is also designed to provide support, protection and resistance to knee flexion contracture. The inner surfaces of the thermoplastic unit may include loop components of hook and loop fasteners for fastening to the outer terry-cloth surface (for example) of the underlying wrap component.

Figure 7A:
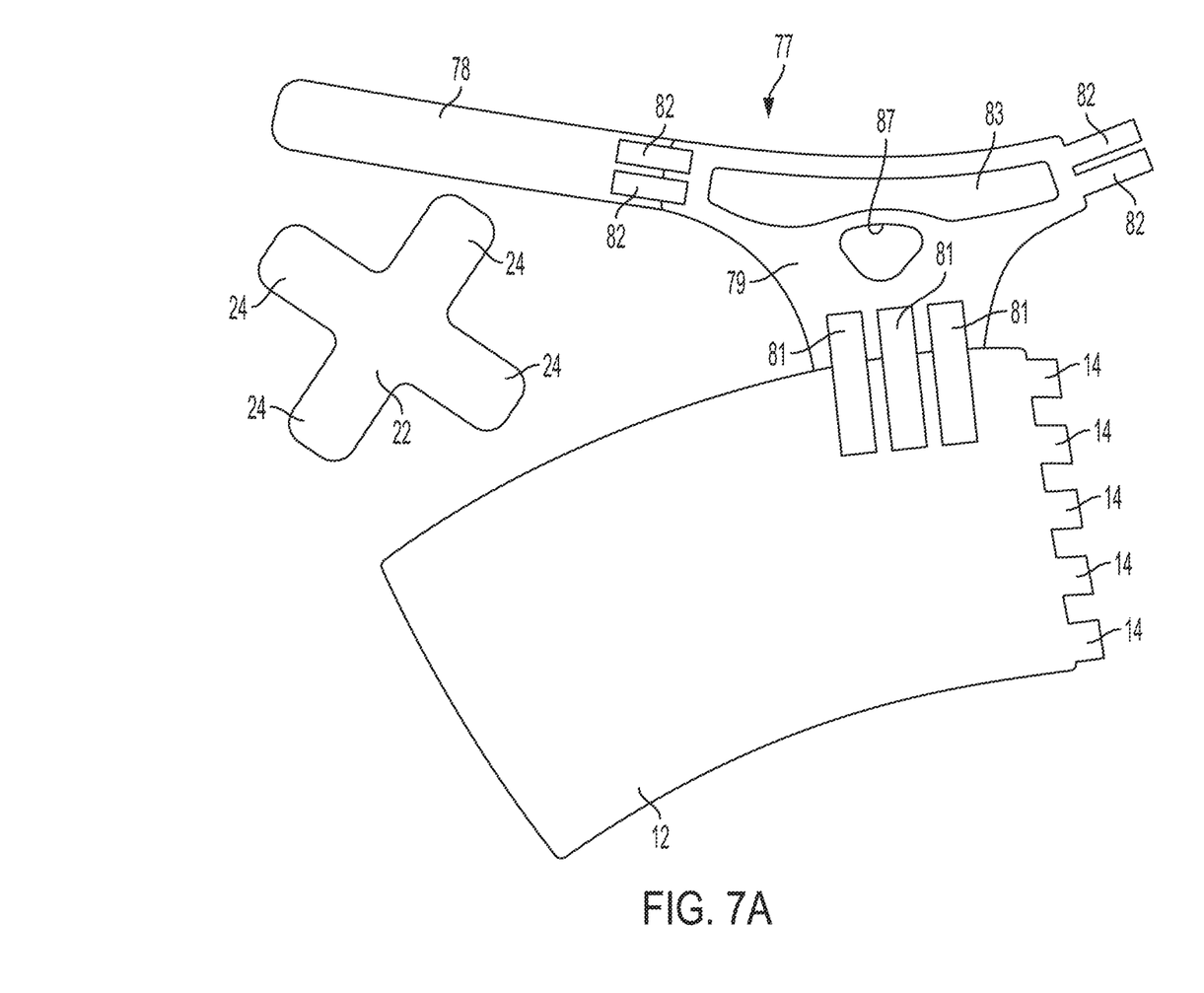
FIG. 7A is an exterior view of a dissembled embodiment of a transfemoral post-operative support apparatus according to the current disclosure.
Figure 7B:
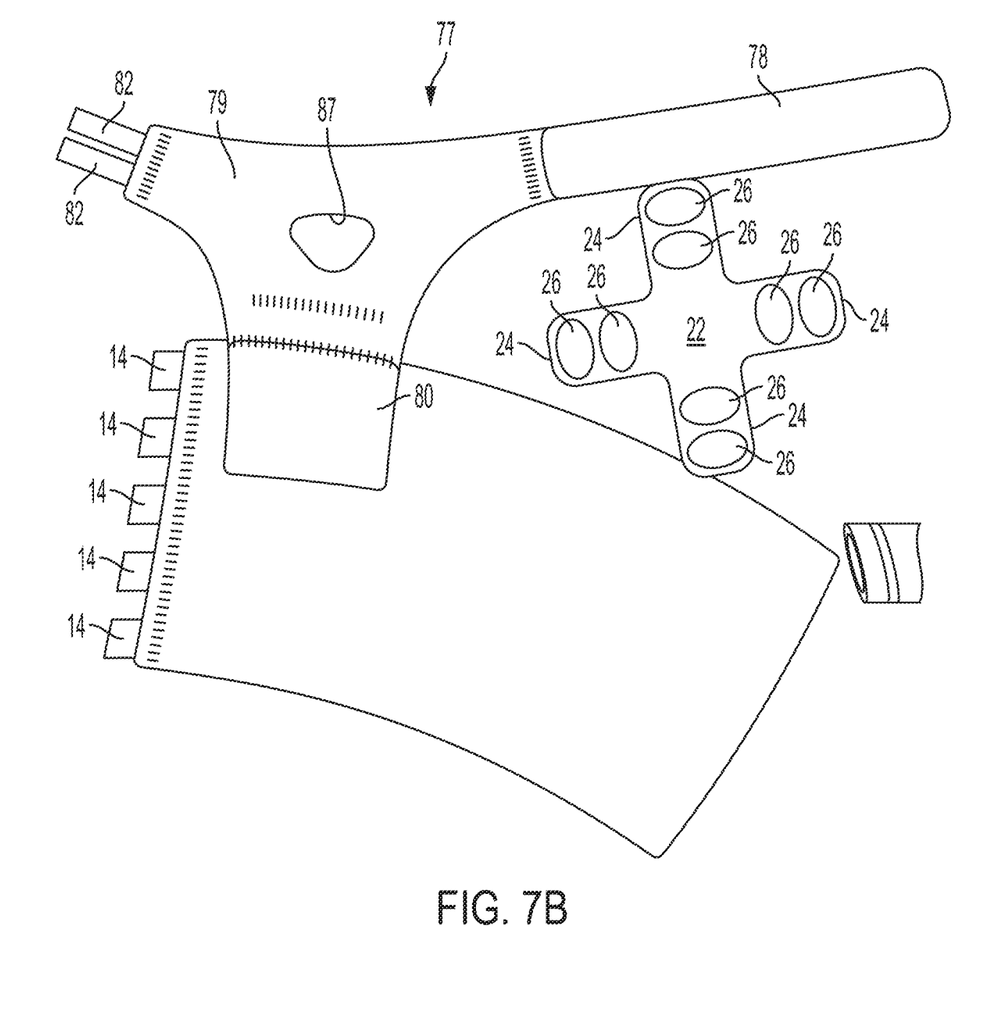
FIG. 7B is an interior view of a dissembled embodiment of a transfemoral post-operative support apparatus of FIG. 7A.
Figure 8:
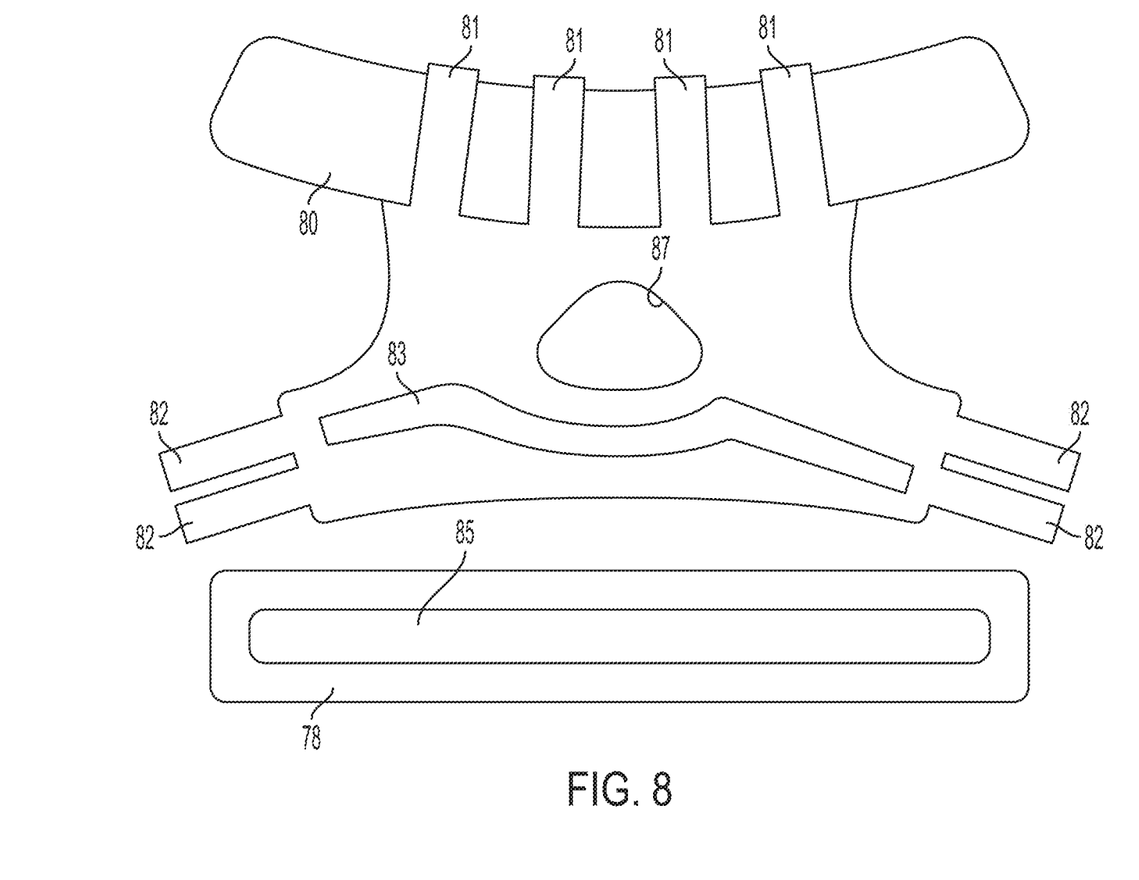
FIG. 8 is an exterior view of an alternate assembly of a transfemoral post-operative support apparatus as disclosed herein.
Figure 9:
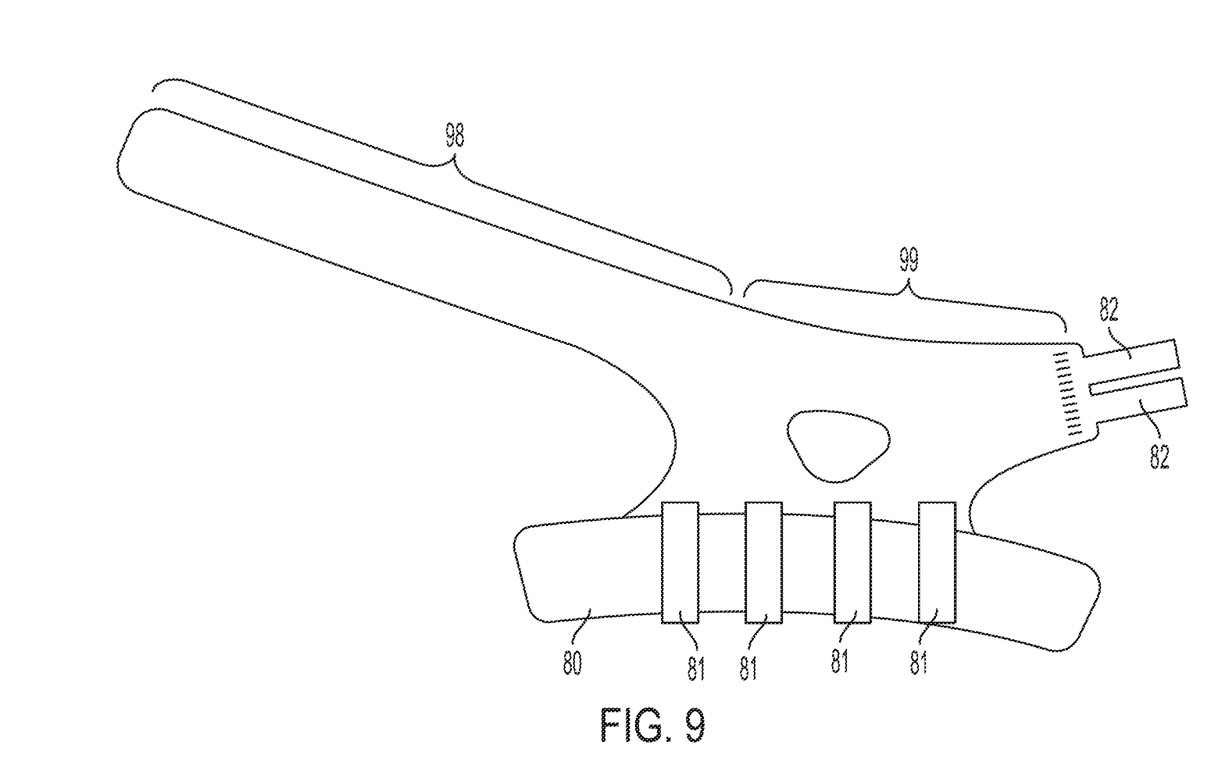
FIG. 9 is an exploded perspective of another alternate assembly of a transfemoral post-operative support apparatus as disclosed herein.

FIGS. 7A and 7B illustrate various components of an alternate example embodiment of a transfemoral post-operative support apparatus according to the current disclosure, as well as various steps for using this embodiment, and donning this embodiment on a patient's residual limb. FIGS. 8 and 9 provide alternate embodiments of the central panel and band panel for use with the post-operative support apparatus as discussed herein.

The transfemoral embodiment of FIGS. 7A and 7B includes a hip-band structure 77 to provide additional support and suspension for the lower wrap panel 12. The hip-band structure 77 includes a generally triangular central panel 79 for orienting about a side of a patient's hip where the wider and upper part (proximal part) of the central panel 79 includes fastening tabs 82 on each proximal corner/end of the central panel 79 for releasably fastening to a waist band panel 78. The generally triangular central panel 79 also includes hook & loop fastening tabs 80 and 81 on the downward pointing part (distal part) for reliably fastening to the wrap panel 12, which is to be wrapped about the patient's residual limb. The larger fastening tab 80 is positioned on the inside while the thinner plural fastening tabs 81 are positioned on the outside of the central panel. In use the fastening tabs 80 & 81 sandwich the wrap panel 12 therebetween. Reinforcing material 83 may be provided on the interior of the triangular central panel 79 about the upper and wider waist-band area of the central panel. A centrally located hole 87 may be provided to register with a patient's hip during donning. As with above embodiments, a flexible and stretchable planar distal panel 22 may be provided to be applied against the distal end of the patient's residual limb (and may include a distal cushion 20 therebetween). As with above embodiments, the flexible, planar distal panel 22 also includes a plurality of flexible legs 24 extending therefrom. Each of the legs have a patch of loop component material 26 fastened to the outer surface.

Figure 10:
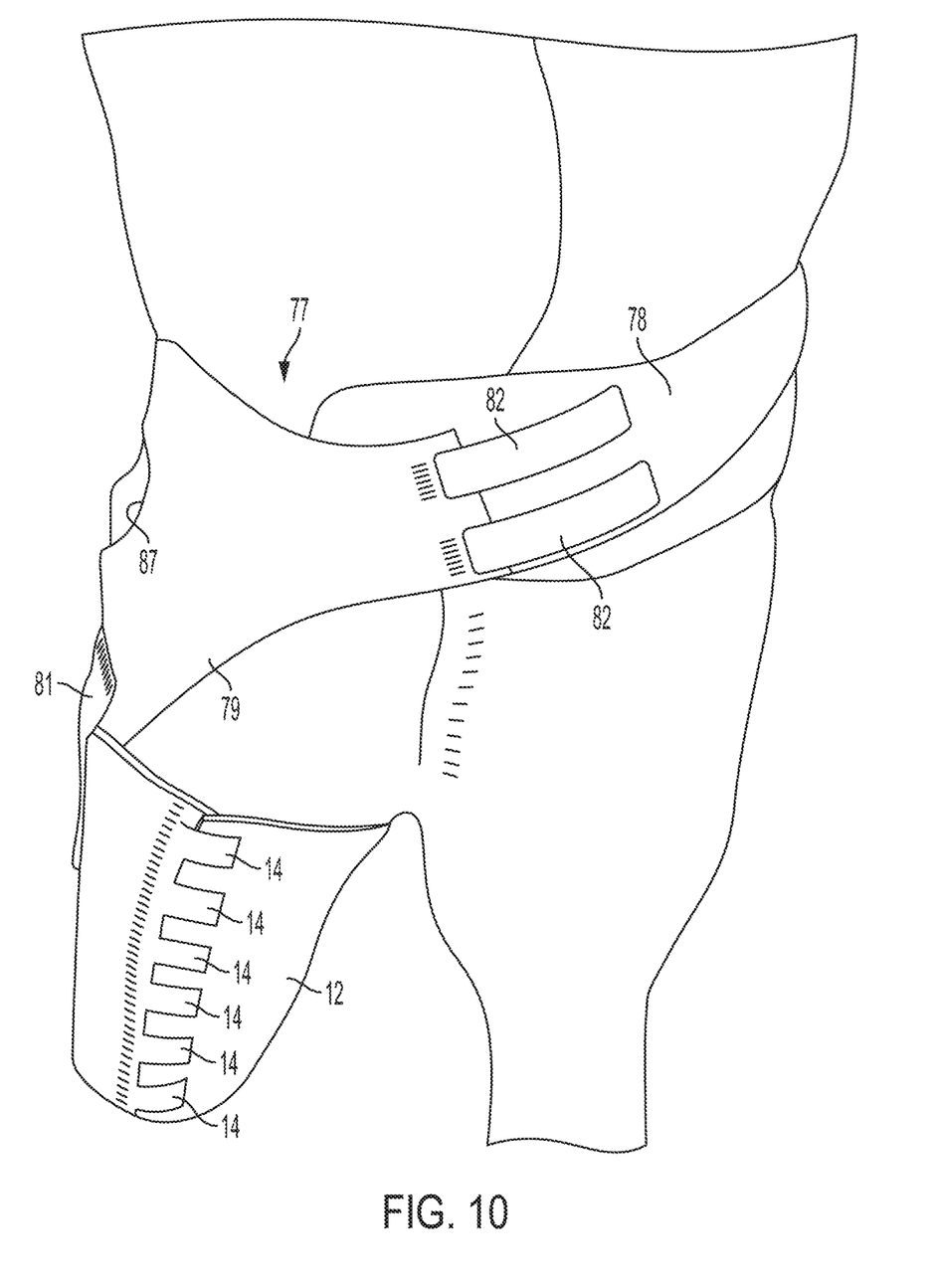
FIG. 10 is an exterior view of the transfemoral post-operative support apparatus of FIGS. 7A and 7B donned on a patient's body.

Referring to FIG. 10, in addition to the steps listed in the disclosure above in relation to donning a wrap panel about a residual limb, the following steps may be performed without regard to particular order in relation to the referenced steps. The waist-band panel 78 and central panel 79 can be sized and trimmed based upon the patient's body dimensions (waist size, torso size, hip size, leg size, leg side, etc.). The waist-band panel 78 is wrapped around the outer circumference of at least a portion of a patient's torso and central panel 79 is placed proximate to the patient's hip of the residual limb so that the fastening tabs 82 are oriented outward and fastening tabs 80 & 81 are oriented downward (distally). Once both the waist-band panel 78 and central panel 79 are in place, the central panel 79 is secured in place wrapping the waist-band panel 78 about the patient's waist and attaching the opposing ends of the waist-band panel 78 to fasteners 82 on opposing lateral ends of the central panel 79. In an embodiment the one or more fasteners 82 may be in the form of a tab extending from at least one of the central panel 79 and the band panel 78, wherein the tab includes one of a hook or loop component configured to fasten to the outer layer of terry cloth material of at least one of the central panel 79 and the band panel 78. As discussed with above embodiments, the wrap panel 12 may be trimmed to adjust to the size of the patient's residual limb. This wrap panel 12 trimming step may occur prior to securing the hip-band structure 77 to the wrap panel 12 via Velcro tabs 80 and 81. A planar distal panel (not shown) may be applied to the distal end of the patient's residual limb with or without a cushion therebetween. It is to be understood that the above steps are not required to be performed in order. It is to be understood that the extension of tabs from and to panels may be reversed or comprise other comparable fastening materials (e.g., buttons, snaps, hooks, zippers, buckles, and the like).

The planar, stretchable and flexible central panel 79 may include one or more tabs 80 & 81 extending from the distal portion of the central panel 79 to the proximal portion of the wrap panel 12 where the tabs include hook components of a hook and loop fastener system (Velcro® fastener), where the loop components will fasten to the outer layer of terry cloth material of the wrap panel 12 to maintain the wrap panel 12 in place relative to the patient's torso. In another embodiment the planar, stretchable and flexible wrap panel 12 may include one or more tabs 81 extending from the proximal portion of the wrap panel 12 to the distal portion of the central panel 79 where the tabs include hook components of a hook and loop fastener system (Velcro® fastener), where the hook components will fasten to the outer layer of terry cloth material of the central panel 79 to maintain the wrap panel 12 in place relative to the patient's torso.

FIG. 8 provides an alternate embodiment of the transfemoral post-operative support in which the outer fastening tab 80 is substantially widened so that it is wrapped around a portion of the patient's residual limb. The widened fastening tab 80 may allow for additional security in primary suspension of the device from falling distally as well as controlling rotation about the residual limb. The widened tab 80 more soundly connects the hip-band structure 77 to the wrap panel 12 thus forming one consistent device when removing and re-applying. Additional reinforcing material 85 may be provided in the waist-band 78. The reinforcement 83, 85 may provide decreased stretch inherently found in the elasticized neoprene embodiments. The reinforcement 83, 85 may also improve connection between the hip-band structure 77 and the wrap panel 12 and may offer more suspension and rotational control. Such reinforcement 83, 85 may be a nylon stitching or an addition of cotton webbing strap, Dacron strapping or a similar component with low inherent material stretch.

FIG. 9 provides an alternate embodiment of the transfemoral post-operative support in which the waist-band is integrated into the central panel. This embodiment provides a single hip-band panel structure including a hip panel portion 99 with similar dimensions of the central panel 79 in above embodiments and a waist-band portion 98 with similar dimensions of the waist-band 78 in above embodiments. With the exception that one end of the waist-band is integrated into the central panel, this embodiment operates generally the same as the above embodiments.

Figure 11:
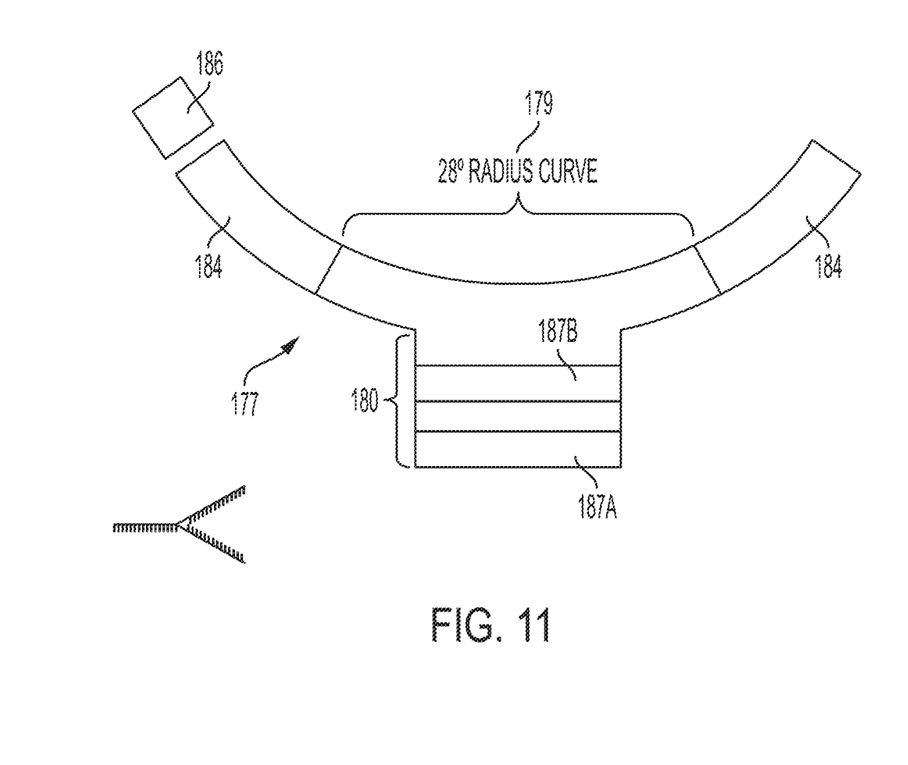
FIG. 11 is an exploded perspective of an alternate assembly of a transfemoral post-operative support apparatus comprising at least a sub-wrap panel with fasteners for use with post-operative support apparatus as disclosed herein.

FIG. 11 provides another alternate embodiment of a hip-band structure 177. In this embodiment, the central panel 179 adapted to seat on a patient's hip is generally t-shaped with a rectangular distally extending outer fastening tab 180 and a pair of laterally extending waist-band extensions 184. The proximal edge (t-portion) of the central panel 179 may have a radius of curvature of about 28 inches, may be about 30 inches in length and may have a vertical width of about 4 inches respectively. The distal edge of the outer fastening tab 180 may be 15 inches in length. The waist-band extensions may be 4 inches vertical width, 15 inches in lateral length each and are not curved. The waist-band extension 184 may comprise a fastener 186 at its longitudinal edge. The fastener 186 may comprise a loop component of a hook and loop system configured to fasten to the corresponding component on the outside or inside of another panel extension or central panel. The fastener may be 4 inches in height and 4 inches in width. Preferably, the fastener is a separate Velcro extension piece for the purpose of fastening one component to another in the process of applying the apparatus.

The outer fastening tab 180 may include one or more fasteners 187A & 187B to fasten to an interior corresponding surface of a hook and loop system of the wrap panel 12 where the fasteners comprise hook components of a hook and loop fastener system (Velcro® fastener), where the loop components will fasten to a corresponding surface comprising a hook or loop component (of a hook and loop system) of the wrap panel 12, to maintain the wrap panel 12 in place relative to the patient's torso and residual limb. In an embodiment, the outer fastening tab 180 may be 7.5 inches in height and 15 inches in width. A first strip 187A of the hook fastening component may be located at the most distal portion of the fastening tab 180. The first strip 187A may be 2 inches in height and 15 inches in width. A second strip 187B of the fastening component may be located 3.5 inches from the distal edge of the sub-wrap panel and 1.5 inches from the proximate edge of the first strip. The second strip 187B may be 2 inches in height and 15 inches in width and may comprise Velcro™.

With all embodiments the various panels and/or tabs 78, 79, 80, 84, 170, 180, 184, etc. may comprise an inner layer of neoprene material and an outer layer of terry cloth material. In the exemplary embodiment, the neoprene material may be nylon lined and perforated (ventilation may promote dissipation of moisture and create airflow to assist in patient comfort).

Having described the various embodiments of the present disclosure in detail and by reference to the attached figures, it will be apparent to those of ordinary skill that the disclosed embodiments are merely current example embodiments and that changes can be made from such embodiments without departing from the scope of the claims. For example, and without limitation, while current embodiments utilize neoprene materials and terry-cloth materials, other suitable materials may be used without departing from the scope of certain claims. For example, and without limitation, a padded nylon construction may be a suitable replacement for the neoprene material used for the wrap panel 12, band panel 78 and/or central panel 79. Further, while current embodiments utilized hook and loop type fasteners, it will be apparent to those of ordinary skill that alternate fasteners (such as buttons, buckles, snaps, zippers, latches, laces, hooks and the like) may be used without departing from the scope of certain claims. Further, while various components may be shown as separate components, it will be apparent to those of ordinary skill that such separate components may be integrated into the apparatus.

It will also be apparent that, while specific dimensions are given for certain exemplary embodiments, such dimensions are only to apply to the specific embodiment and those of ordinary skill will readily understand that changes may be made to any or all of such dimensions without departing from the scope of the claimed subject matter. It will also be apparent to those of ordinary skill that it is not necessary to meet any or all of the stated objects or advantages of the disclosed embodiments to meet any of the recited claims because other un-stated objects or advantages may exist.

What is claimed is:

1. A post-operative support apparatus for a patient's transfemoral residual limb, comprising:
   a planar, stretchable, tensionable and flexible wrap panel sized to wrap around an outer circumference of a patient's transfemoral residual limb, the wrap panel including one or more first fasteners for maintaining the wrap panel in place around the patient's residual limb;
   a planar, stretchable, tensionable and flexible hip-band sized to wrap around an outer circumference of a patient's hip or waist, the hip-band including one or more second fasteners for maintaining the hip-band in place around the patient's hip or waist; and
   one or more third fasteners releasably fastening the wrap panel to the hip-band;
   wherein the one or more third fasteners include an inner fastening tab and at least one outer fastening tab sandwiching the wrap panel therebetween;
   wherein the inner fastening tab is wider than the at least one outer fastening tab;
   where in the hip-band includes a central panel segment configured for orienting about a side of a patient's hip and a waist-band segment for wrapping about the patient's hip or waist;
   wherein the one or more second fasteners releasably fasten a leading end the waist-band segment to the central panel segment;
   wherein the central panel segment includes a distal end width and a proximal end width, the distal end width being larger than the proximal end width;

wherein the inner fastening tab extends the substantially the entire distal end width of the central panel segment; and wherein the inner fastening tab is wider than the distal end width of the central panel segment.

* * * * *